United States Patent [19]

Schmidt et al.

[11] Patent Number: 4,528,384

[45] Date of Patent: Jul. 9, 1985

[54] ADDITION POLYMERIZABLE AROMATIC SULFONIUM SALTS AND POLYMERS THEREOF

[75] Inventors: Donald L. Schmidt; Thomas C. Klingler; Ritchie A. Wessling, all of Midland, Mich.

[73] Assignee: The Dow Chemical Company, Midland, Mich.

[21] Appl. No.: 164,744

[22] Filed: Jun. 30, 1980

[51] Int. Cl.³ .................... C07D 333/16; B05D 1/36
[52] U.S. Cl. .................... 549/78; 549/79; 568/39; 568/54; 568/57; 562/589; 562/598; 562/607; 562/609; 260/504 R; 260/505 R; 260/459 R; 427/411; 427/416
[58] Field of Search .............. 562/589, 598, 607, 609; 260/504 R, 505 R, 459 R; 568/39, 54, 57; 549/78, 79

[56] References Cited

U.S. PATENT DOCUMENTS 3,078,259  2/1963  Hatch et al.
3,409,660  11/1968  Lloyd.
3,775,485  11/1973  Pilgram et al. .................... 568/54
3,903,056  9/1975  Schmidt et al. .................... 549/78
4,111,914  9/1978  Kresta et al.
4,210,552  7/1980  Frenier et al. .................... 568/39

Primary Examiner—Alan Siegel

[57] ABSTRACT

Novel polymers having high activity as cationic surface-active agents are prepared by the addition polymerization of ethylenically unsaturated aromatic sulfonium salts, e.g.,

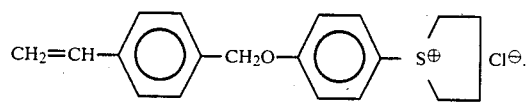

When such polymers are heated and/or dried, they are irreversibly converted to inert, nonionic residues without the elimination of odorous by-products.

The novel sulfonium salt polymers having relatively low molecular weight and low charge density are particularly useful as surfactants or emulsifiers in the emulsion polymerization of ethylenically unsaturated monomers such as styrene, butadiene, alkyl acrylates and the like. The polymers having high molecular weight and high charge density are useful as thickeners and flocculants.

5 Claims, No Drawings

ADDITION POLYMERIZABLE AROMATIC SULFONIUM SALTS AND POLYMERS THEREOF

BACKGROUND OF THE INVENTION

This invention relates to addition polymerizable aromatic sulfonium salts and to their polymers which polymers are useful as surface-active agents.

Organic surface-active agents are widely employed to provide stable aqueous dispersions for such commercial products as paper sizing compositions, floor waxes and polishes, latex paints and many other aqueous coating formulations. In most applications of these products, it is desirable to form a water-resistant protective film by applying the aqueous dispersion to a substrate and then drying the applied dispersion. Unfortunately, however, the desired water-resistance of such film is inherently weakened by the hydrophilic character of the surfactant that is retained in the film.

As shown in U.S. Pat. No. 3,409,660, elimination of lower water resistance caused by residual hydrophilic surfactant has been achieved by employing benzyl sulfonium salts. When polymeric films containing these benzyl sulfonium salts are heated and/or dried, the salt decomposes to form volatile sulfides and a low-molecular weight, non-polymeric hydrophobic residue. Unfortunately, the volatile sulfides have unpleasant odors. In addition, the low-molecular weight residues act as plasticizers and can often be extracted from resulting dried films or coatings; thereby rendering them unsuitable for packaging or otherwise contacting foodstuffs. Thus, use of aqueous dispersions containing these benzyl sulfonium salts is significantly limited.

In view of the aforementioned deficiencies of conventional surface-active agents (e.g., surfactants, emulsifiers and dispersants), it would be highly desirable to provide novel surface-active agents which do not yield hydrophilic residues or odorous vapors when subject to heating and/or drying conditions.

SUMMARY OF THE INVENTION

The present invention is such a surface-active agent. Specifically, in one part, the present invention is a water-soluble, addition polymerizable, ethylenically unsaturated aromatic sulfonium salt represented by the general formula:

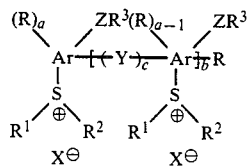
I wherein Ar, R, $R^1$, $R^2$, $R^3$, X, Y, Z, a and b are as defined hereinafter. Hereinafter these salts shall be called ASF salts. Of the ASF salts, the aromatic cyclic sulfonium salts (hereinafter specifically referred to as ACS salts) in which

$R^1$ and $R^2$ are combined in the form of a heterocyclic ring,

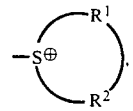

are preferred.

In another aspect, the present invention is a polymer of the aforementioned ASF salt, hereinafter called an ASF polymer. The ASF polymer which is useful as a polymeric surfactant is defined as a substantially linear synthetic polyelectrolyte which is water soluble or water dispersible and has a number average molecular weight ($M_n$) of at least 500 and preferably less than about 40,000, most preferably from about 1,000 to about 7,500. This polyelectrolyte bears a plurality of pendant pH independent cationic groups which are randomly distributed along the backbone of the polyelectrolyte. The backbone of the polyelectrolyte is polyethylenic in that it is advantageously formed by the polymerization of ethylenically unsaturated moieties. Although the pendant ionic groups supply sufficient hydrophilic character and the polyethylenic backbone provides sufficient hydrophobic character to enable the polyelectrolyte to perform as a surfactant, it is understood that the polyelectrolyte may contain other hydrophobic or hydrophilic moieties which are supplied by comonomers other than the ASF salts.

The monomeric form of the ASF salt is particularly useful in the preparation of latex binders for paper coatings and paints wherein the low charge density resulting from the copolymerization of the monomeric salt in the latex polymer (binder) is desired. However, instances wherein relatively high charge density, i.e., non-uniform dispersal of the salt, is required such as paper wet end applications, the preferred surface-active agents are polymeric surfactants which are inherently water-dispersible addition polymers of the aforementioned ASF salts including addition copolymers of the ASF salts with themselves or with other addition copolymerizable monomers.

In the form of polymeric surfactants, the ASF polymer tends to reside more on the surface of the dispersed particles rather than inside the particles, thereby increasing surface charge density. An alternative way to concentrate the ASF polymer on the surfaces of the dispersed solid is to react a sulfonium zwitterion which is a precursor to the ASF salt with the dispersed material having on its surface the remaining polymerized precursor to the ASF salt.

The novel surface-active agents are particularly useful as stabilizing surfactants or emulsifiers in aqueous colloidal dispersions of organic polymers (hereinafter called latexes). In addition, however, these surface-active agents are also useful as wet end additives in the manufacture of paper; as a constituent in polymeric metal coatings, paints and paper coatings; as coadditives with anionic latexes in applications wherein some ionic cross-linking reaction is desired; as a component in water-soluble polymer coating resins; and as a corrosion inhibitor for metals. The high molecular weight, high charge density ASF polymers are particularly useful as thickeners and flocculants. Such salts and their polymers are also useful in many other applications in which fugitive cationic groups are required.

DETAILED DESCRIPTION OF THE ILLUSTRATIVE EMBODIMENTS

In the ASF salts which include the ACS salts, each Ar, as depicted in the aforementioned formula, is individually a cyclic aromatic polyyl which may be mononuclear or polynuclear including fused polynuclear. The term "aromatic polyyl" means a polyvalent aromatic radical having at least one aromatic carbocyclic ring. For example, benzene, a mononuclear aromatic, has a maximum valence of six and naphthalene, a fused polynuclear aromatic, has a maximum valence of eight. Exemplary aromatic polyyls include arenepolyyls, e.g., polyyls of benzene, naphthalene, anthracene and phenanthrene; as well as fused carbocyclic/heterocylic aromatic polyyls, e.g., quinoline, isoquinoline, acridine, benzoquinoline, 1-azophenanthrene, benzofuran and benzothiophene. Of the aromatic polyyls, the arenepolyyls are preferred, with polyyls of benzene being most preferred.

Each R is individually a suitably inert monovalent moiety which is capable of existing as a substituent on Ar. The term "suitably inert moiety" means a moiety that is inert to the cyclic sulfonium and ethylenically unsaturated moieties and does not prevent addition polymerization of the ASF salt. In the ACS salts, R also does not prevent the polymerization of the ACS salt or addition polymers thereof through the cyclic sulfonium moiety. Examples of R include H, X wherein X is halogen such as Cl, OH, R', OR', SR', and

OCR' wherein R' is hydrocarbyl or inertly substituted hydrocarbyl. Hydrocarbyl is a monovalent hydrocarbon radical, e.g., one having 1 to 20 carbons. Preferably hydrocarbyl is alkyl, cycloalkyl, alkenyl, aryl, alkylaryl, aralkyl and similar hydrocarbon radicals having 1 to 8 carbons. Exemplary substituents of substituted hydrocarbyl include X, OH, OR', SR' and the like wherein X and R' are as defined hereinbefore. Preferably R is hydrogen, hydroxyl, $C_1-C_{16}$ alkyl, and $C_1-C_{16}$ alkoxy, with hydrogen and $C_1-C_{10}$ alkyl being especially preferred.

In the ASF salts, each $R^1$ and each $R^2$ are individually suitably inert monovalent organic moieties and/or each $R^1$ and $R^2$ are collectively a suitably inert divalent organic moiety capable of forming a heterocyclic ring with

When each $R^1$ and each $R^2$ are individually a suitably inert monovalent organic moiety, each is advantageously hydrocarbyl or substituted hydrocarbyl as set forth in the definition of R. Suitable examples include alkyl, aryl, cycloalkyl, alkylaryl, alkylthioalkyl, alkoxyalkyl and the like. Preferred are aryl and alkylaryl such as phenyl and tolyl or $C_1-C_{16}$ alkyl wherein the carbons in the position alpha to

are preferably methylene or methyl. Examples of preferred alkyls include methylethyl, propyl, butyl or octyl, with the most preferred being $C_1-C_4$ alkyls.

In the ACS salts, the cyclic sulfonium moiety,

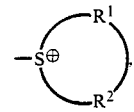

is advantageously a 5- to 7-membered heterocyclic ring that is a ring substituent of a carbocyclic aromatic ring of Ar, most often a ring substituent of the same aromatic ring that bears $-ZR^3$ as a ring substituent. Preferably, the cyclic sulfonium moiety is a 5- or 6-membered ring usually substituted in a ring position on Ar that is ortho or para to the $-ZR^3$ substituent. Of the preferred cyclic sulfonium moieties, the 5-membered rings are especially preferred. In ACS salts wherein $R^1$ and $R^2$ are collectively any suitably inert divalent organic moiety ($-R^1R^2-$) that can exist in a heterocyclic ring containing sulfur, $-R^1R^2-$ should not contain bulky and/or reactive groups that would (1) prevent the formation of the stable cyclic sulfonium moiety on Ar, or (2) deleteriously affect the ability of the

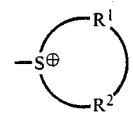

to undergo a ring-opening reaction. Accordingly, $-R^1R^2-$ is most advantageously hydrocarbylene or inertly substituted hydrocarbylene wherein hydrocarbylene is a divalent hydrocarbon moiety such as alkylene. Alternatively, $-R^1R^2-$ is suitably heterohydrocarbylene or substituted heterohydrocarbylene wherein the chain of the hydrocarbon is interrupted by a hetero atom, e.g., oxygen or sulfur. Hydrocarbylene and heterocarbylene are of sufficient length to provide a 5- to 7-membered ring including

In all suitable $-R^1R^2-$, the two carbons of $-R^1R^2-$ bonded to

are methylene. Exemplary suitable hydrocarbylenes and heterohydrocarbylenes include alkylene, cycloalkylene, alkenylene, alkylenearylenealkylene, alkyleneoxyalkylene, and alkylenethioalkylene. When $-R^1R^2-$ is substituted hydrocarbylene or substituted heterohydrocarbylene, suitable substituents include monovalent radicals given in the definition of R such as OH, R', OR', and SR' wherein R' is hydrocarbyl. Preferably, —R¹R²— is a hydrocarbylene such as —(CH₂)₄—; —(CH₂)₅—;

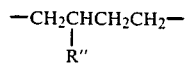

wherein R″ is C₁-C₄ alkyl or aryl, such as phenyl or alkylaryl such as tolyl,

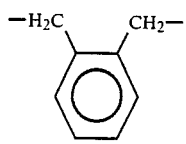

or heterohydrocarbylene such as —(CH₂)₂—O—(CH₂)₂—; with —(CH₂)₄— and

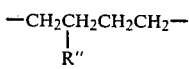

being especially preferred.

In the definition of R¹ and R² it is understood R¹ and R² can be the same or different monovalent organic moieties in an ASF salt molecule. Also R¹ and R² can be taken collectively as a divalent moiety in one sulfonium moiety and individually as monovalent organic moieties in another sulfonium moiety wherein both sulfonium moieties reside in an ASF salt molecule.

Each R³ is individually an ethylenically unsaturated, monovalent organic radical which is capable of undergoing addition polymerization. Representative examples of R³ include vinylhydrocarbyl such as vinylbenzyl including substituted vinylbenzyl and allyl including substituted allyl such as 2-ethenylallyl; alkenylcarbonyl such as α,β-ethylenically unsaturated carbonyl, e.g., acryloyl and methacryloyl; alkenylcarbonyloxyalkylenyl such as acryloylethylenyl; alkenylcarbonylaminoalkylenyl such as acrylamido; alkenyloxycarbonylalkylenyl such as vinyloxycarbonylmethylenyl and the like. Of the foregoing, R³, vinylbenzyl and methacryloyl are preferred with vinylbenzyl being most preferred.

Y is a suitably inert divalent radical capable of bridging aromatic rings each bearing ring-substituted —ZR³ and cyclic sulfonium cation. Suitable examples of Z include —O—, —S—,

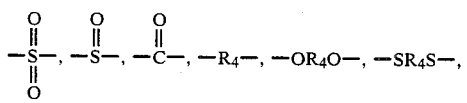

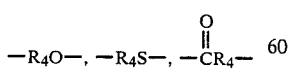

and the like wherein R₄ is hydrocarbylene or substituted hydrocarbylene with substituents as defined for R. Advantageously, R₄ is hydrocarbylene having 1-8, especially 2-4, carbons. Preferably, Y is —S—, —O—, alkylene, arylene, or oxyalkyleneoxy. Especially preferred are —O(C$_m$H$_{2m}$)O—,

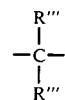

or —CH₂— wherein m=1-4 and R‴=C₁-C₄ alkyl.

X⊖ is an anion, for example, halide such as chloride or bromide; saturated carboxylate such as acetate, formate, or lactate; unsaturated carboxylate such as acrylate; bicarbonate; sulfate; dihydrogenphosphate; alkyl aryl and alkyl aryl sulfonate such as benzene sulfonate; and another suitably inert anion; with acetate, lactate and chloride being preferred. While the ASF salt is normally made having a halide as the anion, this halide anion is readily exchanged by conventional means, e.g., ion exchange resin, to carboxylate, bicarbonate, etc. In applications wherein metal corrosion is a problem, carboxylate such as acetate is preferred over chloride.

Z is a divalent oxygen or sulfur moiety, preferably a divalent oxygen moiety. The letter "a" is a positive number corresponding to the number of remaining available ring positions on Ar; "b" is 0 or a positive number, usually from 1 to 2, preferably b is 0 or 1; and "c" is 0 or 1.

Exemplary preferred ACS salts are represented by the following formulae:

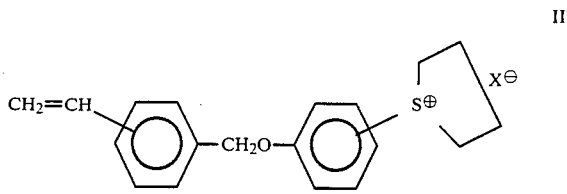

II

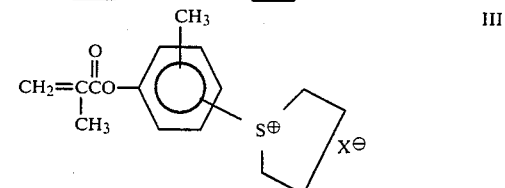

III

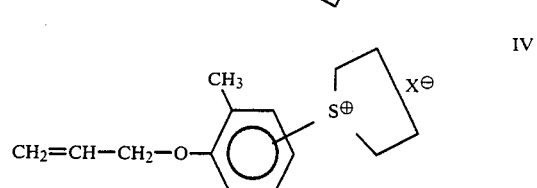

IV

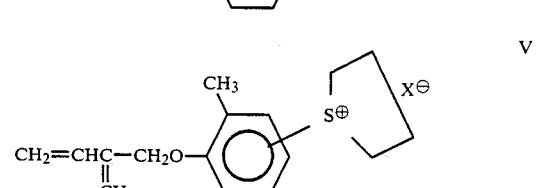

V

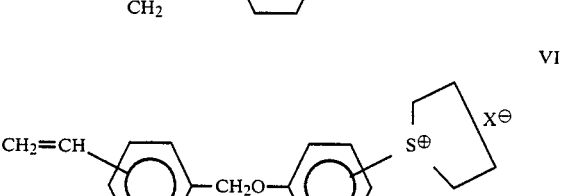

VI

-continued

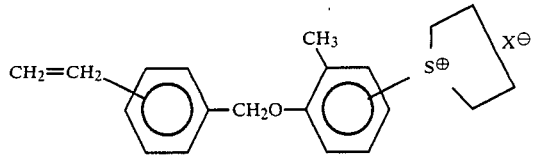
VII

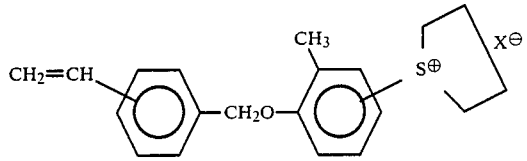
VIII

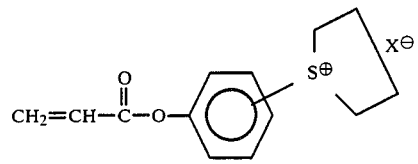
IX

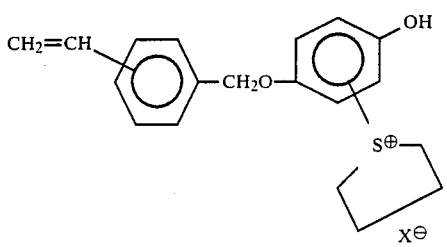
X

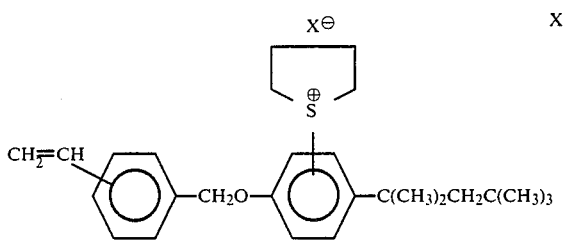
XI wherein X is chloride or carboxylate such as acetate, lactate or acrylate. Of the foregoing ACS salts, those represented by formulae III and VII are especially preferred.

Exemplary suitable ASF salts which do not contain cyclic sulfonium groups include those represented by the following formulae:

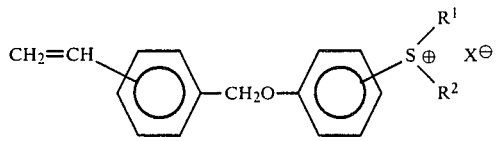
XII

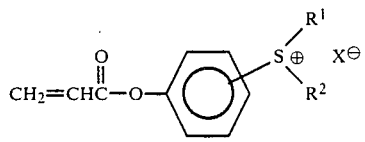
XIII

-continued

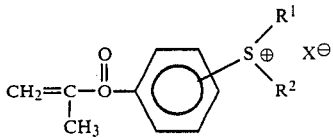
XIV wherein $R^1$ and $R^2$ are individually methyl, ethyl, propyl, butyl, hydroxyethyl; and X is chloride or carboxylate such as acetate, lactate or acrylate. In addition, when $R^1$ is methyl, $R^2$ can be alkyl having up to 16 carbons.

The ASF salts of the present invention are advantageously prepared by reacting an aromatic sulfonium zwitterion with the desired ethylenically unsaturated precursor.

The aromatic sulfonium zwitterions and methods for their preparation are described in detail in U.S. Pat. Nos. 3,636,052; 3,660,431; 3,723,386; 3,749,737; 4,118,297 and Ser. No. 673,579 filed Apr. 5, 1976, all of which are hereby incorporated by reference.

Examples of desired ethylenically unsaturated precursors include vinylbenzyl chloride, allyl chloride, 3-chloromethyl butadiene-1,4, acryloyl chloride, methacryloyl chloride, maleic anhydride, citraconic anhydride, benzene sulfonate ester of 2-hydroxyethyl acrylate and the like. Methods for preparing these precursors are well known and therefore will not be described here.

The reaction of zwitterion and ethylenically unsaturated precursor is advantageously carried out in a polar solvent, preferably water, at temperatures in the range from about 45° to about 70° C. Other suitable polar solvents include methanol, ethanol and isopropyl alcohol. While the relative proportions of reactants and concentrations of reactions in the polar solvent are not particularly critical, the zwitterion and ethylenically unsaturated precursor are advantageously employed in stoichiometric proportions and in concentrations in the polar solvent ranging from about 5 to about 40 weight percent of each reactant based on the total reaction mixture. Following complete mixing of the reactants, it is desirable to heat the reaction mixture at a temperature in the range from about 45° to about 70° C., preferably from about 50° to about 60° C., most preferably from about 53° to about 58° C. for a period in the range from about 1 to about 8, preferably from about 5 to about 8, hours to insure complete reaction. The resulting ASF salt is readily recovered from the reaction mixture by conventional procedures, e.g., as described hereinafter in the examples.

The ASF salt is ready to be employed in monomeric form as a dispersing surfactant in an aqueous dispersion of addition polymerizable monomers. Also, the ASF salt can be employed in solution polymerization wherein water or other polar liquid such as an alcohol is employed as solvent and other soluble comonomers are optionally present thereby forming other useful polymers. Alternatively, the ASF salt can be homopolymerized or copolymerized with one or more suitable monomers and employed in the form of a low molecular weight polymer, e.g., $M_n$ less than about 40,000, as a dispersing surfactant in a wide variety of aqueous dispersions wherein water-immiscible liquids or water-insoluble solids are dispersed in a continuous aqueous phase.

When the ASF salt is employed in monomeric form, it is preferably used as a cationic comonomer in an emulsion polymerization process wherein water-insoluble emulsion polymerizable monomers are dispersed in an aqueous phase containing an appropriate catalyst and subjected to emulsion polymerization conditions. Suitable monomers and emulsion polymerization conditions are reported in Blackley's *Emulsion Polymerization*, Halstead Press of John Wiley & Sons, (1975), which is hereby incorporated by reference in its entirety.

Exemplary emulsion polymerizable monomers preferably employed in combination with the ASF salts include the following hydrophobic ethylenically unsaturated monomers: monovinylidene aromatic hydrocarbons, e.g., styrene, α-methylstyrene, ar-methylstyrene, ar,ar-dimethylstyrene, vinyl naphthalene, ar-ethylstyrene, and ar-(t-butyl)styrene as well as derivatives thereof bearing non-ionic substituents, e.g., ar-cyanostyrene, ar-chlorostyrene, ar-bromostyrene, ar-hydroxystyrene, ar-methoxystyrene, and vinylbenzyl chloride; conjugated dienes, e.g., butadiene and isoprene; the unsaturated alcohol esters such as vinyl acetate and vinyl propionate; the unsaturated ketones, e.g., vinyl methyl ketone and methyl isopropenyl ketone; the unsaturated ethers, e.g., vinyl ethyl ether and vinyl methyl ether; and the nonionic derivatives of ethylenically unsaturated carboxylic acids such as acrylic esters, e.g., methyl acrylate, ethyl acrylate, butyl acrylate, hexyl acrylate, 2-ethylhexyl acrylate and lauryl acrylate; methacrylic esters, e.g., methyl methacrylate, ethyl methacrylate; the maleic esters such as dimethyl maleate, diethyl maleate and dibutyl meleate; the fumaric esters, e.g., dimethyl fumarate, diethyl fumarate and dibutyl fumarate and the itaconic esters, e.g., dimethyl itaconate, diethyl itaconate and dibutyl itaconate; the nitriles, e.g., acrylonitrile and methacrylonitrile; and ethylenically unsaturated halides, e.g., vinyl chloride, vinyl bromide and vinylidene chloride. Also, monomers which form water-soluble homopolymers, e.g., acrylamide, methacrylamide, aminoethyl acrylate, sulfoethyl methacrylate, acrylic acid, methacrylic acid, itaconic acid, maleic anhydride; hydroxyethyl acrylate and hydroxyethyl methacrylate, may be mixed with a hydrophobic monomer in amounts such that the resulting polymer retains the ability to exist as colloidal size particles when dispersed in water or other aqueous medium, usually less than about 30 weight percent, preferably less than about 10 weight percent based on the weight of the polymer. Of the aforementioned monomers, the ASF salts are preferably copolymerized with styrene, butadiene and the acrylate esters. The resulting latex is at least partially stabilized by the presence of the cationic sulfonium moieties which are chemically bound to the emulsion polymerizate (latex polymer). Accordingly, there are sufficient sulfonium moities in the latex polymer to enable the polymer to exist as colloidal-sized particles which are uniformly dispersed in an aqueous medium without the aid of external surfactants and/or emulsifiers. Advantageously, the sulfonium moieties are present in an amount in the range from about 0.01 to about 0.6, preferably from about 0.03 to about 0.4, most preferably from about 0.07 to about 0.3, milliequivalents per gram (meq/g) of latex polymer (dry basis).

In the preparation of latexes by the aforementioned method, it should be understood that the ASF salt may be added at any time during the emulsion polymerization procedure. In fact, it is sometimes preferred to delay addition of the ASF salt to the emulsion polymerization recipe until most of the monomers are converted to polymers, thereby concentrating the ASF salt in the outer portion of the individual latex particles. Such concentration of ASF salt in the outer portion of latex particle can be further accentuated by employing in the emulsion polymerization recipe a seed latex containing little or none of the ASF salt. Such a method for preparing latexes having core/shell latex particles of varying polymeric composition are described in U.S. Pat. Nos. 2,520,959; 3,397,165 and 4,056,501, which are hereby incorporated by reference in their entirety.

Alternatively, the ASF salt can be first polymerized or copolymerized and then employed in polymeric form (as a so-called cationic polymeric surfactant hereinafter called ASF polymeric surfactant) to stabilize emulsion polymerization recipes as well as a wide variety of other aqueous dispersions. In polymeric form, the ASF salt can exist as a homopolymer or as a copolymer with one or more other ASF salts and/or other copolymerizable monomers, e.g., a water-insoluble emulsion polymerizable monomer as defined hereinbefore, a water-soluble monomer such as an unsaturated acid or amide, e.g., acrylic acid and acrylamide; hydroxyalkyl esters, sulfoalkyl esters and aminoalkyl esters of ethylenically unsaturated carboxylic acids; and other water-soluble copolymerizable monomers. Of the various ASF polymeric surfactants, the copolymers of the ASF salts with hydrophobic comonomers such as styrene and alkyl styrenes, the conjugated dienes, nonionic esters of unsaturated carboxylic acids including the alkyl and hydroxyalkyl esters are preferred. The copolymers containing residual function groups or residual unsaturation which is available for further polymerization are most preferred. Examples of such copolymers containing residual unsaturation including copolymers of the ASF salts with conjugated dienes, e.g., butadiene; alkenyl esters of unsaturated carboxylic acids, e.g., dicyclopentadienyl acrylate; and other copolymerizable polyethylenically unsaturated compounds having ethylenically unsaturated groups which are different in regard to ability to polymerize such as diallylmaleate and the like. Examples of copolymers containing residual functional groups include copolymers of the ASF salts with hydroxyalkyl esters of ethylenically unsaturated carboxylic acids, e.g., hydroxyethyl acrylate, hydroxypropyl acrylate and hydroxyethyl methacrylate; ethylenically unsaturated isothiouronium salts; epoxy alkyl esters of ethylenically unsaturated acids such as glycidyl acrylate; and other copolymerizable monomers bearing reactive functional moieties that are water insensitive and do not react with the sulfonium moiety of the ASF salts. Examples of such functional groups include hydroxy, epoxy, isothiouronium, amino, chlorobenzyl, and the like. Further examples of such functional comonomers include 2-aminoethyl methacrylate, vinylbenzyl chloride, vinylbenzyl isothiouronium chloride and the like.

In the preferred ASF polymeric surfactants, the polymerized ASF salt should be present in concentrations sufficient to render the polymer water-soluble. By "water-soluble" is meant that the polymer will form a thermodynamically stable mixture with water. These mixtures form spontaneously and include true solutions wherein the individual polymer molecules are dispersed as well as micellar or colloidal solutions wherein the polymer molecules are aggregated to some extent. Preferably, such polymers have relatively low charge densities, i.e., contain from about 1 to about 4, most preferably from about 1.4 to about 2.5, milliequivalents of sulfonium moiety per gram of polymer. The preferred copolymers also contain sufficient hydrophobic moiety to enable the copolymer to adsorb on the surface of the emulsion polymerizable monomer and/or the emulsion polymerization (latex polymer).

The residual unsaturation and/or reactive functionality present in the most preferred copolymers should be of type and amount sufficient to render the copolymer copolymerizable with and/or reactive with monomers of an emulsion polymerization recipe under conditions of emulsion polymerization. Usually amounts of polyethylenically unsaturated comonomers and/or functional comonomers are those sufficient to provide at least one unsaturated and/or functional group per molecule of ASF copolymer molecule, preferably at least two of such groups per molecule. Of course, it is understood that a somewhat higher concentration of said groups, i.e., at least two groups per copolymer molecule, should be employed if the group has a low reactivity, e.g., allylic unsaturation, or if the ASF copolymer has a lower molecular weight, e.g., $M_n$ less than 10,000. Normally, from about 0.025 to about 8, preferably from about 0.1 to about 4, milliequivalents of the polyethylenically unsaturated comonomer and/or the functional comonomer per gram of the copolymer is employed to produce the aforementioned desired concentration of unsaturation and/or functional groups which thereby insures the formation of a chemical bond between the ASF copolymer and the latex polymer during the emulsion polymerization. It is further understood that it is desirable to match the reactivities of the ethylenically unsaturated moieties of the ASF polymer with those of the monomers to be subjected to emulsion polymerization in order to maximize copolymerization of said emulsion polymerizable monomer(s) with the ASF polymer. For example, allyl unsaturation should be matched to allyl unsaturation and monovinylidene aromatic to the same or acryloyl.

The molecular weight of the ASF polymeric surfactant is such that (1) it can function as a stabilizing surfactant or emulsifier during and after the emulsion polymerization and (2) it will sufficiently contact the emulsion polymerizable monomer and/or latex polymer such that a chemical bond between the ASF copolymer (polymeric surfactant) and the latex polymer is formed. Advantageously, the $M_n$ of the ASF polymeric surfactant as determined by destroying sulfonium moieties and measuring molecular weight of nonionic derivative(s) by gel permeation chromatography using polystyrene standard is less than about 40,000 (e.g., from about 500 to about 40,000), preferably less than about 10,000 (e.g., from about 1,000 to about 10,000), most preferably less than about 7,500 (e.g., from about 1,000 to about 7,500).

The ASF polymeric surfactants are readily prepared by subjecting an appropriate monomeric mixture of ASF salt and other comonomer(s) to conventional addition polymerization conditions. For example, a monomer mixture of the ACS salt and other desired comonomer(s) dispersed in sufficient water or other polar solvent to provide a monomer concentration from about 15 to about 25 weight percent is stirred under an atmosphere of nitrogen or similar inert gas and heated to a temperature in the range from about 45° to about 75° C. in the presence of a chain transfer agent and an initiating amount of a free-radical generating initiator. Exemplary other polar solvents which are advantageously mixed with water include aliphatic alcohols such as methanol, ethanol and isopropanol; glycols and glycol ethers such as ethylene glycol and diethylene glycol methyl ether; and other polar organic solvents that are inert to the reactants of the copolymerization reaction. It is understood, however, that there is no need to use compatibilizing solvent when the ASF monomer is sufficiently surface active to emulsify the comonomer in water. Exemplary free radical initiators include peroxygen initiators such as hydrogen peroxide; organic peroxides such as t-butyl peroxide, benzoyl peroxide, perbenzoic acid, etc., which are often activated by water-soluble reducing agents such as ferrous compounds, sodium bisulfite and hydroxylamine hydrochloride; organic hydroperoxides such as cumene hydroperoxide and t-butyl hydroperoxide; as well as other free radical generating initiators such as azo compounds, e.g., 2,2-azobisisobutyronitrile. Exemplary chain transfer agents are the low molecular weight halohydrocarbons such as carbon tetrabromide and bromoform, mercaptans such as ethyl mercaptan and mercapto alkanols such as 2-mercaptoethanol, with the latter being preferred.

In the preparation of a latex, the ASF polymeric surfactant is dispersed or dissolved in the aqueous medium in which the emulsion polymerizable monomer is to be dispersed and polymerized. The resulting emulsion polymerization recipe is then subjected to conditions of conventional emulsion polymerization. See, for example, Blackley's *Emulsion Polymerization,* supra. When the ASF polymeric surfactant contains residual unsaturation, it copolymerizes with the emulsion polymerizable monomer(s), and is thereby grafted onto the latex polymer. On the other hand, when the ASF polymeric surfactant contains functional groups that are reactive with functional groups on the emulsion polymerizable monomer or the latex polymer, the ASF functional group reacts to form the desired chemical bond. By delaying addition of the ASF polymeric surfactant to the emulsion polymerization recipe until a substantial amount or all of polymerization has occurred and/or by controlling other polymerization conditions, e.g., increased concentration of chain transfer agent or increased ASF polymeric surfactant to monomer ratio, etc., the ASF polymeric surfactant can be concentrated in the outer regions of the latex particle. The ASF polymeric surfactant can also be concentrated in the outer regions (near surface regions) of the latex particle by forming a seed latex using the ASF polymeric surfactant and a small amount of emulsion polymerizable monomer(s) and add remaining monomer(s) to form final latex from seed latex.

Alternative to employment of an ASF polymeric surfactant to concentrate it on the surface of the dispersed solid, the dispersed solid containing a polymerized reactive precursor to the ASF salt can be reacted with the sulfonium zwitterion precursor to form the desired polymerized ASF salt. For example, a latex of a polymer containing polymerized vinylbenzyl chloride can be reacted with a sulfonium zwitterion such as 4-tetrahydrothiophenium phenoxide. The resulting latex exhibits stability and charge density comparable to one prepared by polymerizing monomers in the presence of an ASF polymeric surfactant. However, because this process requires more time and is less efficient in terms of reacting and utilizing all sulfonium zwitterion added to the system, it is generally not as desirable as the aforementioned emulsion polymerization carried out in the presence of an ASF polymeric surfactant.

The ASF polymeric surfactants of this invention are suitably employed to stabilize a wide variety of other aqueous dispersions such as low molecular weight resins, e.g., melamine resins; clay and other inorganic particulates and the like.

In dispersion applications, the ASF polymeric surfactant is advantageously dispersed in an aqueous medium in an amount sufficient to disperse or to stabilize a dispersion of a material that does not inherently form stable dispersions when placed in the aqueous medium. This stabilizing amount of ASF polymeric surfactant is preferably from about 0.5 to about 15, most preferably from about 3 to about 10 weight percent, based on the dry weight of the dispersed material.

Polymers of ASF salts can be dissolved or dispersed in water, applied as coatings and dried to form useful films, adhesives, binders and the like. When such ASF polymers are contacted with anion exchange resins to convert the salt to hydroxide or bicarbonate and then contacted with dicarboxylic acid, a crosslinkable composition results. Copolymers of approximately equivalent mole ratios of ASF salts and $\alpha,\beta$-ethylenically unsaturated acids such as acrylic acid can be converted to zwitterions by contacting aqueous solutions of such copolymers with cation exchange resins. Such zwitterions can be cross-linked to form protective coatings by drying and/or heating.

By employing the ASF monomer(s) alone or a combination of the ASF monomer(s) and water-soluble or very hydrophilic comonomers and by substantially increasing the molecular weight of the ASF polymer to values of $M_n$ greater than 40,000, said polymers, which are preferably water soluble, are effective flocculants for a wide variety of suspensions and dispersions, particularly those wherein the suspended particles bear an anionic charge. Advantageously, such high molecular weight polymers have $M_n$ from about 40,000 to about 15 million or more. Some high molecular weight ASF polymers also have relatively high charge densities, i.e., they contain from about 2 to about 5, preferably from about 2.5 to about 4, milliequivalents of sulfonium moiety per gram of the ASF polymer. These high molecular weight, high charge density ASF polymers are also useful additives in the manufacture of paper, e.g., as retention aids and wet and dry strength additives. Other polymers of the ASF salts which contain copolymerized nonionic water-soluble monomers such as acrylamide and have relatively low charge densities, e.g., from 0.1 to about 2 milliequivalents of sulfonium moieties per gram of ASF polymer, are useful wet strength resins.

The following examples are given to further illustrate the invention and utilization thereof and should not be construed as limiting the scope of the invention. In the following examples all parts and percentages are by weight, unless otherwise specified.

EXAMPLE 1

A. Preparation of Aromatic Cyclic Sulfonium Salt (ACS)

Vinylbenzyloxy-4-(2-methylphenyl)tetrahydrothiophenium Chloride (2-VBTHC)

(1) A 122.1-g (0.8 mole) portion of vinylbenzyl chloride (VBC), isomeric mixture containing 60 percent of meta-isomer and 40 percent of para-isomer is added with stirring to a solution of 92 g (0.40 mole) of 2-methyl-4-tetrahydrothiophenium phen-1-oxide.dihydrate (2-MTHTP) dissolved in 118.8 g (155 ml) of methanol. While mixing, the resulting reaction mixture is heated at 55° C. for 4 hours. A 200-ml portion of water is then added to the reaction mixture, and the mixture is extracted three times with 150-ml portions of hexane. A portion of the hexane and methanol are removed under vacuum to yield 324 g of product solution (31 percent solids) containing 100.4 g (72.4 percent yield) of solid 2-MTHTP which is found by NMR analysis to have the following structure:

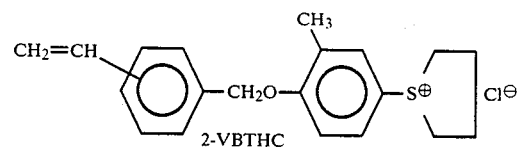

(2) Following a similar procedure, a 166-g (1.09 mole) portion of VBC is added to a solution of 125 g (0.543 mole) of 2-MTHTP and 5 g of 2-VBTHC in 150 g of water. This mixture is heated at 55° C. with vigorous stirring for 5.5 hours. Then 200 g of water is added to the mixture and extracted three times with 150-ml portions of hexane. The remaining hexane is removed under vacuum to yield 416.6 g of solution containing 150.8 g of 2-VBTHC (80.1 percent yield).

B. Latex Preparation

Into a 250-ml citrate bottle are weighed the following ingredients:

| Ingredient | Amount, Parts |
| --- | --- |
| 2-VBTHC | 4 |
| Deionized Water | 294 |
| Styrene | 65 |
| 30% Active $H_2O_2$ in $H_2O$ | 1.67 |
| 0.1% Active $FeCl_3.6H_2O$ in $H_2O$ | 1.1 | which are then purged with nitrogen while held in an ice bath. A 35-part portion of cooled butadiene is added. The bottle is capped and tumbled at 70° C. for 17 hours. A clean fluid latex is recovered containing 25.3 percent solids (theoretical solids is 26 percent), no waste, 0.147 milliequivalents of charge per gram of solids. Charge on the resulting latex particles is determined by titration of $Cl^\ominus$ wherein titration is corrected for acid. Conversion of monomer to polymer is 97.3 percent. A layer of the latex is cast on a glass substrate and dried at 110° C. to provide a water-insensitive film. No odor is observed during drying.

EXAMPLES 2–7

Following the procedure (1) of Example 1 for preparation of an ACS salt, several ACS salts specifically described in Table I are prepared. These salts are recovered and employed in emulsion polymerization recipes comparable to that described in Example 1.

TABLE I

| Example No. | ACS Salt (1) Zwitterion | ACS Salt (1) Unsaturated Precursor | ACS Salt (1) % Active | Initiator (2) Type | Initiator (2) Amount % | Additional Emulsifier (3) Type | Additional Emulsifier (3) Amount % | Latex % ACS Salt | Latex % Solids | Latex % Conversion |
|---|---|---|---|---|---|---|---|---|---|---|
| 2 | 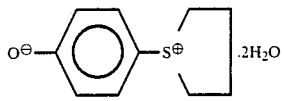 | VBC | | $H_2O_2$ | 0.5 | — | | 2 | 25.2 | 93 |
| 3 | THTP.2H$_2$O | VBC | | $H_2O_2$ | 0.5 | — | | 4 | 25.3 | 94 |
| 4 | 4-HTHTP | VBC (a) | | AZO | 0.5 | DBSC | 2 | 2 | 23.8 | 93 |
| 5 | ar-NTHTP | VBC | 7.18 | $H_2O_2$ | 0.5 | — | | 2 | 23.8 | 93 |
| 6 | 2-MTHTP.2H$_2$O | AC (b) | 61.3 | $H_2O_2$ | 0.5 | DBSC | 1 | 2 | 25.1 | 99 |
| 7 | 2-MTHTP.2H$_2$O | 2-CMB (c) | 35.5 | AZO | 1 | | | 2 | 22.9 | 90 |

THTP.2H$_2$O — 4-tetrahydrothiophenium phen-1-oxide dihydrate

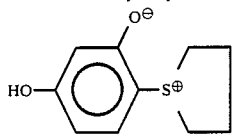

4-HTHTP — 4-hydroxy-2-tetrahydrothiophenium phen-1-oxide

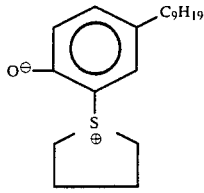

ar-NTHTP — 4-nonyl-2-tetrahydrothiophenium phen-1-oxide

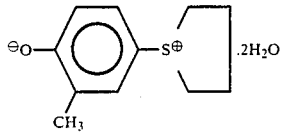

2-MTHTP.2H$_2$O — 2-methyl-4-tetrahydrothiophenium phen-1-oxide dihydrate

VBC — vinylbenzyl chloride (60/40 mixture of meta- and para-isomers)
AC — allyl chloride
2-CMB — 2-(chloromethyl)butadiene
(a) First procedure of Example 1 is followed except 116.3 g (0.5 mole) of 2,4-dihydroxyphenyl tetrahydrothiophenium chloride in 600 ml of methanol is combined with sodium methoxide until a pH of 10.5 is reached. The resulting NaCl is removed by filtration and 182.6 g (1.2 mole) of VBC is added. A 300-ml portion of H$_2$O is added to the reaction product which is then extracted with hexane as indicated in Example 1.
(b) First procedure of Example 1 is followed except 115 g (0.5 mole) of 2-MTHTP.2H$_2$O is combined with 150 g (1.96 mole) of allyl chloride, 0.4 g of KI in 400 ml of methanol and heated at 50° C. for 30 hours.
(c) First procedure of Example 1 is followed except that 92 g (0.4 mole) of 2-MTHTP.2H$_2$O in 150 ml of methanol is added to 69.2 g (0.67 mole) of 2-(chloromethyl)butadiene. About 5 mg of 2-methyl-2,4-dinitrophenol is added to the reaction mixture and the resulting mixture is maintained at 42° C. for 3 days. A 100-ml portion of H$_2$O is added to the reaction product which is then extracted with hexane as indicated in Example 1.
(2) $H_2O_2$ — 30% active hydrogen peroxide
AZO — 100% active azobis(isobutyro)nitrile
Weight percent of 100% initiator based on weight of monomer
(3) DBSC — 25% Active dodecylbenzyl dimethyl sulfonium chloride As evidenced by the data shown in Table I for Example Nos. 2, 3, 5 and 7, no added emulsifier is required to stabilize the resulting latex. Moreover, by determining surface charge density for the resulting latexes before and after subjecting the latexes to dialysis using a regenerated cellulose membrane, it is found that the latexes retained a major portion of their original surface charge density. This retention of charge density indicates substantial copolymerization of the ACS salt into the latex polymers.

EXAMPLE 8

Using the ACS salt of Example 1, a copolymer of the ACS salt with methyl methacrylate (MMA) is prepared by adding 54.7 parts of an aqueous solution (39.7 percent active) of the ACS salt and 3.28 parts of MMA (ACS/MMA mole ratio of 2:1) to a 280 ml citrate bottle containing 40.1 parts of deionized water. To this mixture is added 0.888 part of a 30 percent active aqueous solution of H$_2$O$_2$, 0.592 part of 0.1 percent active aqueous solution of FeCl$_3$.6H$_2$O and 0.382 part of 2-mercaptoethanol. The citrate bottle is shaken and maintained at 75° C. for 2 hours. The resulting homogeneous solution contains 28.5 percent of an ACS/MMA (2/1) copolymer having an M$_n$ as determined by gel permeation chromatography of ~4000.

Into a 1-liter polymerization flask added with stirring are the following ingredients:

| | Dry Wt., Parts | Wet Wt., Parts |
|---|---|---|
| ACS/MMA (2/1) copolymer (25%) | 10 | 40 |
| Deionized Water | | 260.2 |
| H$_2$O$_2$ (30%) | 1.5 | 5.00 |
| FeCl$_3$.6H$_2$O (0.1%) | .0333 | 3.33 |

| | Dry Wt., Parts | Wet Wt., Parts |
|---|---|---|
| Styrene | 45 | 45 |
| Methyl Methacrylate | 45 | 45 |
| 1N HCl (pH 3.5–4.0 in combined mixture) | | 1.5 |

The flask containing the stirred mixture of these ingredients is placed in a hot water bath (75° C.–77.5° C.) for one hour during which time the temperature of the ingredients increased from 68.5° C. to 85.5° C. (peak) and cooled to 74.7° C. The resulting fluid latex (26.1 percent solids) (100% conversion) is rub stable wherein rub stability is determined by the rub stability test described in U.S. Pat. No. 4,056,501. The charge on the latex polymer as determined by titration for chloride ion is 0.27 meq/g of latex polymer (dry basis).

EXAMPLES 9–11

Following procedure (1) of Example 1, three acyclic ASF salts are prepared by reacting acyclic aromatic sulfonium zwitterions specified in Table II with vinylbenzyl chloride. The resulting ASF salts are employed in the latex preparation procedure of Example 1 and the results are reported in Table II.

TABLE II

| Example No. | ASF Salt (1) | | % Active | Initiator (2) | | Latex | | |
|---|---|---|---|---|---|---|---|---|
| | Zwitterion | Unsaturated Precursor | | Type | Amount % | % ASF Salt | % Solids | % Waste |
| 9 | DMSMP | VBC | 57 | AZO | 0.5 | 2 | 16.6 | 3.3 |
| 10 | DDSMP | VBC | 63 | AZO | 0.5 | 2 | 22.4 | <1 |
| 11 | DESMP | VBC | 52.1 | AZO | 0.5 | 2 | 18.8 | 1.8 |

(1) DMSMP — 2-methyl-4-(dimethylsulfonium)phen-1-oxide

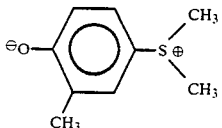

DDSMP — 2-methyl-4-(dodecylmethylsulfonium)phen-1-oxide

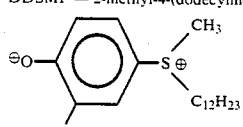

DESMP — 2-methyl-4-(diethylsulfonium)phen-1-oxide

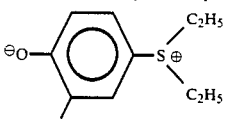

(2) Same as (2) in Table I

When the latexes of the foregoing Example Nos. 1–7 containing ACS polymers are applied as coatings to a substrate (wood, paper, metal, glass) by conventional coating techniques and cured by drying under ambient conditions, a tough coating is formed which exhibits substantially less sensitivity to water than coatings prepared from similar latexes containing conventional cationic emulsifiers. No volatiles other than water are detected during the curing process.

While coatings prepared from latexes of Example Nos. 9–11 containing polymers having acyclic sulfonium moieties emit some volatiles other than water during cure, they do not emit noticeable sulfide odors. Coatings prepared from said acyclic sulfonium polymers also exhibit somewhat greater sensitivity to water than do those prepared from cyclic sulfonium polymers, e.g., as in Examples 1–7.

EXAMPLE 12

Into a 250 ml citrate bottle are added 40 g of styrene, 60 g of butyl acrylate and 4.5 g of 2-VBTHC used in Example 1. To the resulting mixture is added a 2.1-g portion of methacryloyl chloride which is agitated at room temperature for 10 minutes. An orange gel forms to which is added a 300-g portion of water thereby forming an emulsion.

The emulsion is transferred to a one liter polymerization reactor and purged with nitrogen. Hydrogen peroxide (0.48 g of a 30 percent active solution) and ferric ion solution (0.32 g of 0.1 percent $FeCl_3.6H_2O$ in water) are added to the reactor which is then heated to 60° C. Two additional portions of the aforementioned $H_2O_2$/$Fe^{+3}$ initiator (each of which are equivalent to the initial portion) are added at 20 minute intervals to the reactor. After six hours at 60° C., the reaction mixture is cooled and recovered as a clean fluid latex (20.4 percent solids, average particle size of 0.152 micrometer). The latex polymer is found to contain 0.095 milliequivalent (meq) of polymerized sulfonium ion per gram of polymer solids.

EXAMPLE 13

Into a 2 gallon Pflaudler Kettle are added with stirring 1156 g of 30 percent active solution of 2-VBTHC in water (347 g of 2-VBTHC) which also contains 3.51 percent of unreacted zwitterion precursor, 36 g of 30 percent active $H_2O_2$, 24 g of ferric ion solution (0.1 percent $FeCl_3.6H_2O$ in water), 805 g of water adjusted to pH of 3.5 with diluted HCl and 15.6 g of 2-mercaptoethanol. The kettle is closed and purged with nitrogen. A 162-g portion of butadiene is charged to the kettle and the temperature is brought to 75° C. and maintained for 3 hours and 35 minutes. The kettle is cooled to room temperature and the resulting polymeric surfactant is recovered as a 23.8 percent solids solution of a butadiene/2-VBTHC (3:1 mole ratio) copolymer having a $M_n$ as determined by GPC of 5472 and 1.83 meq of sulfonium ion per gram of polymer.

To a 250 ml citrate bottle are charged 28.4 g of the aforementioned reaction product containing 6.76 g of the polymeric surfactant, 128.2 g of deionized water adjusted to pH of 3.5 with dilute HCl, 0.12 g of 30 percent active $H_2O_2$, 0.08 g of ferric ion solution (0.1 percent $FeCl_3.6H_2O$ in water), 25.9 g of styrene and 17.3 g of butadiene. The reaction vessel is purged with nitrogen, agitated and heated to 75° C. for 4 hours. The reaction product is cooled to room temperature and recovered as a latex (22.7 percent polymer solids, 0.1410 micrometer particle size). The latex is subjected to dialysis using regenerated cellulose as permeable membrane and is found to retain surface charge equivalent to 0.194 meq of sulfonium ion per gram of latex polymer. This retention of surface charge indicates that the polymeric surfactant is nondesorbable, i.e., is bound to the particle.

EXAMPLE 14

Into a 250 ml citrate bottle are charged 36 g of deionized water adjusted to pH of 3.5 with diluted HCl, 145.8 g of 23.8 percent solution of 2-VBTHC in water containing 3.4 g of unreacted zwitterion precursor, 5.41 g of butadiene (B), 7.06 g of acrylic acid (AA), 2.71 g of 30 percent active $H_2O_2$, 1.81 g of the ferric ion solution used in Example 13 and 1.17 g of 2-mercaptoethanol. The bottle is purged with nitrogen and heated to 75° C. for 2 hours while agitating the bottle in a steam-heated tumbler at 24 rpm. The resulting product is 23.3 percent polymer solid solution of 2-VBTHC/butadiene/acrylic acid terpolymer (mole ratio 1:1:1) wherein the terpolymer contains 1.97 meq of sulfonium ion per gram of terpolymer. This terpolymer can be converted to zwitterion form wherein the sulfonium moiety is the cation and the carboxylate group of polymerized acrylic acid is the anion by passing the polymer solution through an anion exchange resin capable of removing $Cl^{\ominus}$. In zwitterion form the terpolymer is useful as a cross-linkable polymer suitable for coating applications.

Following the procedure of this example, several polymers are prepared from different ratios of the same monomers and are listed in Table III. The resulting polymers are recovered and tested for charge density and coating properties. The results are reported in Table III.

TABLE III

| Monomer Mole Ratio 2-VBTHC/B/AA | $HSCH_2CH_2OH$ Mole % (1) | % Solids (2) | Charge, Meq $S^+/g$ (3) | Coating Properties (4) |
| --- | --- | --- | --- | --- |
| 1:1:1 | 5 | 23.3 | 1.97 | Tough, leathery |
| 1:0:1 | 5 | 22.0 | 2.16 | Hard |
| 1:3:1 | 5 | 22.5 | 1.66 | Soft, elastic |

(1) Same as (2) in Table IV.
(2) Weight percent of 2-VBTHC/B/AA copolymer based on weight of coating formulation.
(3) Same as (4) in Table IV.
(4) The ion exchanged polymer solutions are applied to cold rolled steel test panels to form coatings. After drying and heating at ~100° C., the resulting cross-linked coatings are clear, glossy and adherent to the metal surface. They are very hydrophobic and water resistant. No sulfur odors are detected in the drying and curing process.

EXAMPLE 15

Following the procedure of Example 14, several polymers are prepared using other combinations of monomers and are tested for water solubility and charge density. The results are reported in Table IV. These polymers are useful as retention aids in paper making.

TABLE IV

| | | | | Polymer | |
| --- | --- | --- | --- | --- | --- |
| Sample No. | Monomers (1) Type | Mole Ratio | $HSCH_2CH_2OH$ Mole % (2) | % Solids (3) | Charge Density Meq $S^+$/gm Polymer (4) |
| 1 | 2-VBTHC/B/HEA | 1:1:1 | 0 | 7.46 | 1.83 |
| 2 | 2-VBTHC/B/HEA | " | 5 | 23.2 | 1.96 |
| 3 | 2-VBTHC/B/AAM | " | 0 | 22.0 | 2.14 |
| 4 | 2-VBTHC/B/AAM | " | 5 | 21.8 | 2.10 |
| 5 | 2-VBTHC | | 0 | 16.1 | 2.44 |
| 6 | 2-VBTHC/B/AAM | 1:1:1 | 0 | 22.0* | 2.14 |
| 7 | 2-VBTHC/B/AAM | " | 5 | 21.8* | 2.10 |

*A small amount (<5 weight percent) of water-insoluble material is removed by filtration prior to measurement of % solids.
(1) 2-VBTHC — vinylbenzyloxy-4-(2-methylphenyl)tetrahydrothiophenium chloride
B — butadiene
AA — acrylic acid
AAM — acrylamide
HEA — hydroxyethyl acrylate
(2) mole percent of 2-mercaptoethanol based on total monomers
(3) Same as (2) in Table III.
(4) Charge density in milliequivalents of sulfonium ion per gram of polymer on a dry basis. Charge density determined by titration for chloride ion.

EXAMPLE 16

Into a 2 gallon Pflaudler Kettle is charged 2236 g of 30.5 percent active solution of 2-VBTHC, 924 g of deionized water, 120 g of 1N HCl, 5.35 g of thiourea and 36.8 g of 2-mercaptoethanol. The kettle is purged with nitrogen, closed and charged with 318 g of butadiene. The kettle is then heated to 50° C. and charged with 160 g of 3 percent active $H_2O_2$. This temperature is maintained for a period of 2 hours during which is ~1.7 g portion of 3 percent active $H_2O_2$ is charged to the kettle at one-minute intervals. The reaction mixture is maintained at 50° C. for an additional 3 hours after which the mixture cools to room temperature. A 25 percent active solution of 2-VBTHC/butadiene copolymer (1:3 mole ratio) having a $M_n$ of 4,212, $M_w$ of 10,501 and 1.85 meq of sulfonium moiety per g of copolymer is recovered.

It is observed that the foregoing procedure employing the combination of thiourea and hydrogen peroxide as initiator is a preferred method for preparing the ASF polymers at low temperatures, e.g., less than 60° C.

What is claimed is:

1. A water-soluble, addition polymerizable ethylenically unsaturated aromatic sulfonium salt represented by the formula:

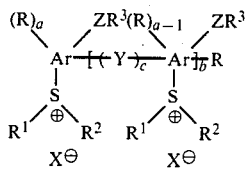

wherein each Ar is individually a cyclic aromatic polyyl, each R is independently a suitably inert monovalent moiety capable of existing as a substituent on Ar, each $R^1$ and each $R^2$ are individually suitably inert monovalent organic moieties and/or each $R^1$ and $R^2$ are collectively a suitably inert divalent organic moiety which forms a heterocyclic ring with

each $R^3$ is individually an ethylenically unsaturated monovalent organic radical which is capable of undergoing addition polymerization, each Y is individually a suitably inert divalent radical capable of bridging aromatic moieties, each Z is individually a divalent sulfur or divalent oxygen, each $X^\ominus$ is a suitably inert anion, a is a positive number corresponding to the number of remaining available ring positions on Ar, b is 0, 1 or 2, and c is 0 or 1.

2. The salt of claim 1 represented by the formula:

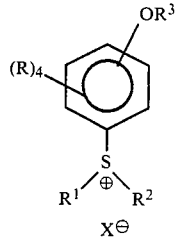

wherein each R is individually H, Cl, OH, R', OR', SR', or

in which R' is hydrocarbyl or inertly substituted hydrocarbyl; each $R^1$ and each $R^2$ are individually hydrocarbyl or inertly substituted hydrocarbyl or $R^1$ and $R^2$ are collectively hydrocarbylene, inertly substituted hydrocarbylene, heterohydrocarbylene or inertly substituted heterohydrocarbylene; $R^3$ is vinyl hydrocarbyl or alkenylcarbonyl; and $X^\ominus$ is saturated carboxylate, unsaturated carboxylate, bicarbonate, sulfate, dihydrogen phosphate, hydrocarbyl sulfonate or halide.

3. The salt of claim 2 wherein R is H, OH or alkyl having 1 to 8 carbons, each $R^1$ and each $R^2$ are individually alkyl or $R^1$ and $R^2$ are collectively butylene or pentylene, $R^3$ is vinylbenzyl, acryloyl or methacryloyl and $X^\ominus$ is chloride, acetate or lactate.

4. The salt of claim 3 which is represented by one of the following formulae:

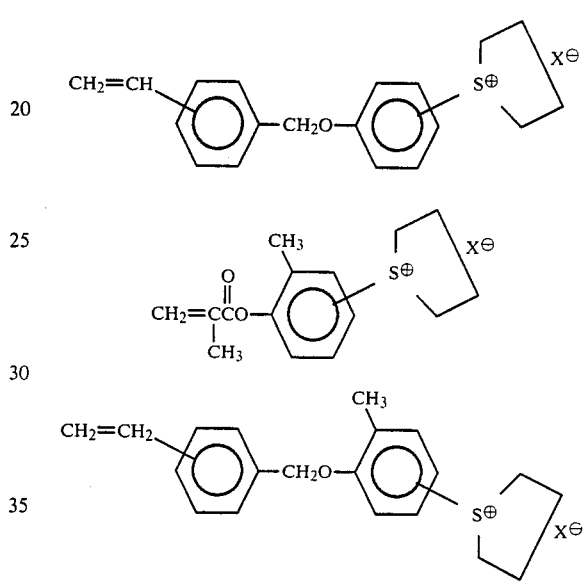

5. The salt of claim 1 which is represented by the formula:

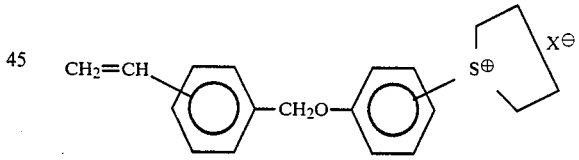

wherein $X^\ominus$ is chloride, acetate or lactate.

* * * * *